US011350949B2

(12) United States Patent
Sitry et al.

(10) Patent No.: US 11,350,949 B2
(45) Date of Patent: Jun. 7, 2022

(54) MULTIPLE HEAD DRILL

(71) Applicant: T.A.G. Medical Products Corporation Ltd., Kibbutz Gaaton (IL)

(72) Inventors: Hagay Sitry, Haifa (IL); Hagay Botansky, Haifa (IL); Ran Weisman, Kfar-Vradim (IL); Rotem Barak, Nahariya (IL); Roy Zilberman, Qadarim (IL)

(73) Assignee: T.A.G. Medical Products Corporation Ltd., Kibbutz Gaaton (IL)

( * ) Notice: Subject to any disclaimer, the term of this patent is extended or adjusted under 35 U.S.C. 154(b) by 390 days.

(21) Appl. No.: 16/332,812

(22) PCT Filed: Sep. 18, 2017

(86) PCT No.: PCT/IL2017/051053
§ 371 (c)(1),
(2) Date: Mar. 13, 2019

(87) PCT Pub. No.: WO2018/051356
PCT Pub. Date: Mar. 22, 2018

(65) Prior Publication Data
US 2019/0201012 A1    Jul. 4, 2019

Related U.S. Application Data

(60) Provisional application No. 62/396,182, filed on Sep. 18, 2016.

(51) Int. Cl.
*A61B 17/16* (2006.01)
*A61B 90/00* (2016.01)

(52) U.S. Cl.
CPC ...... *A61B 17/1617* (2013.01); *A61B 17/1615* (2013.01); *A61B 17/1631* (2013.01); *A61B 17/1675* (2013.01); *A61B 2090/062* (2016.02)

(58) Field of Classification Search
CPC . A61B 17/16; A61B 17/1615; A61B 17/1617; A61B 17/164; A61B 17/1662;
(Continued)

(56) References Cited

U.S. PATENT DOCUMENTS 5,908,423 A * 6/1999 Kashuba .............. A61B 17/164
606/80
6,197,031 B1 * 3/2001 Barrette .............. A61B 17/155
606/311
(Continued)

FOREIGN PATENT DOCUMENTS

EP    1785103    5/2007
EP    1836977    9/2007
WO   WO 2018/051356  3/2018

OTHER PUBLICATIONS

Communication Pursuant to Article 94(3) EPC dated Nov. 26, 2021 From the European Patent Office Re. Application No. 17777976.6. (6 Pages).

(Continued)

*Primary Examiner* — Eric S Gibson

(57) ABSTRACT

A drill device including a shaft having a proximal end and a distal end, one or more first reaming heads configured to be positioned along the shaft adjacent the distal end and one or more second reaming heads configured to be positioned along the shaft at a location axially proximally spaced from the first reaming head.

39 Claims, 16 Drawing Sheets

(58) Field of Classification Search
CPC .......... A61B 17/1664; A61B 17/1668; A61B 17/1675
See application file for complete search history.

(56) References Cited

U.S. PATENT DOCUMENTS

| | | | | |
|---|---|---|---|---|
| 9,498,230 B2* | 11/2016 | Smith | ............... | A61B 17/1617 |
| 9,687,252 B2* | 6/2017 | Kelman | ............... | A61B 17/164 |
| 10,912,572 B2* | 2/2021 | Kunz | ............... | A61C 8/0089 |
| 2004/0267267 A1* | 12/2004 | Daniels | ............... | A61F 2/3662 |
| | | | | 606/80 |
| 2006/0264956 A1* | 11/2006 | Orbay | ............... | A61B 17/1615 |
| | | | | 606/80 |
| 2010/0217267 A1* | 8/2010 | Bergin | ............... | A61B 17/1668 |
| | | | | 606/80 |
| 2011/0015634 A1* | 1/2011 | Smith | ............... | A61B 17/164 |
| | | | | 606/80 |
| 2011/0112540 A1* | 5/2011 | McLean | ............ | A61B 17/1617 |
| | | | | 606/80 |
| 2014/0081271 A1 | 3/2014 | Whittaker et al. | | |
| 2014/0100576 A1* | 4/2014 | Smith | ............... | A61B 17/1617 |
| | | | | 606/80 |
| 2015/0190147 A1 | 7/2015 | Ferragamo et al. | | |
| 2015/0320427 A1* | 11/2015 | Kelman | ............ | A61B 17/1668 |
| | | | | 606/80 |
| 2015/0342617 A1* | 12/2015 | Kunz | ............... | A61C 1/14 |
| | | | | 433/75 |
| 2017/0035442 A1* | 2/2017 | Smith | ............... | A61B 17/164 |
| 2017/0281311 A1* | 10/2017 | Aloise | ............... | A61B 17/1617 |
| 2017/0290596 A1* | 10/2017 | Kelman | ............... | A61B 17/164 |
| 2019/0201012 A1* | 7/2019 | Sitry | ............... | A61B 17/1617 |
| 2020/0375615 A1* | 12/2020 | Walker | ............... | A61B 17/1764 |
| 2021/0196285 A1* | 7/2021 | Hathaway | ............ | A61B 17/921 |

OTHER PUBLICATIONS

International Preliminary Report on Patentability dated Mar. 28, 2019 From the International Bureau of WIPO Re. Application No. PCT/IL2017/051053. (11 Pages).

International Search Report and the Written Opinion dated Feb. 12, 2018 From the International Searching Authority Re. Application No. PCT/IL2017/051053. (19 Pages).

\* cited by examiner

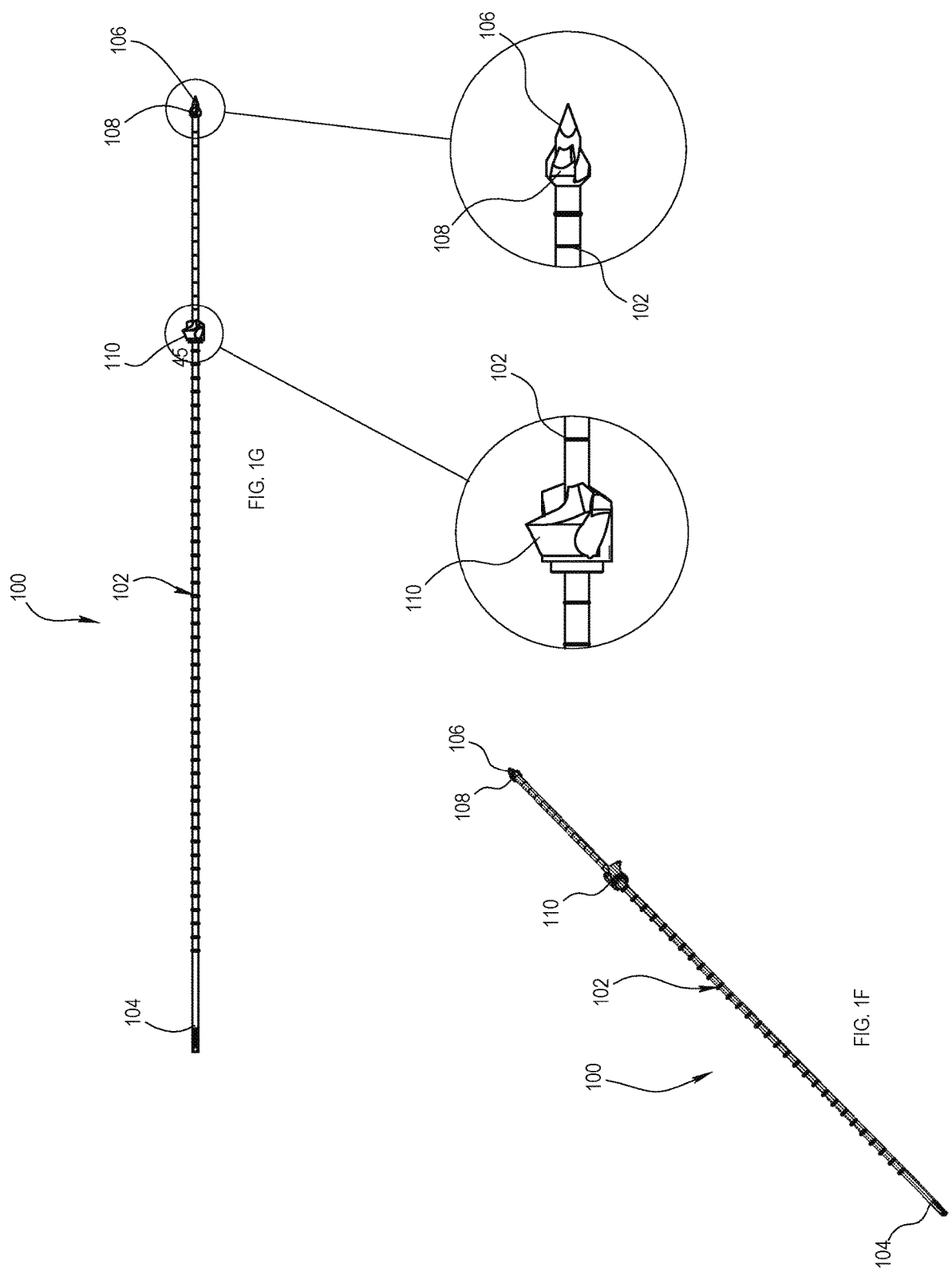

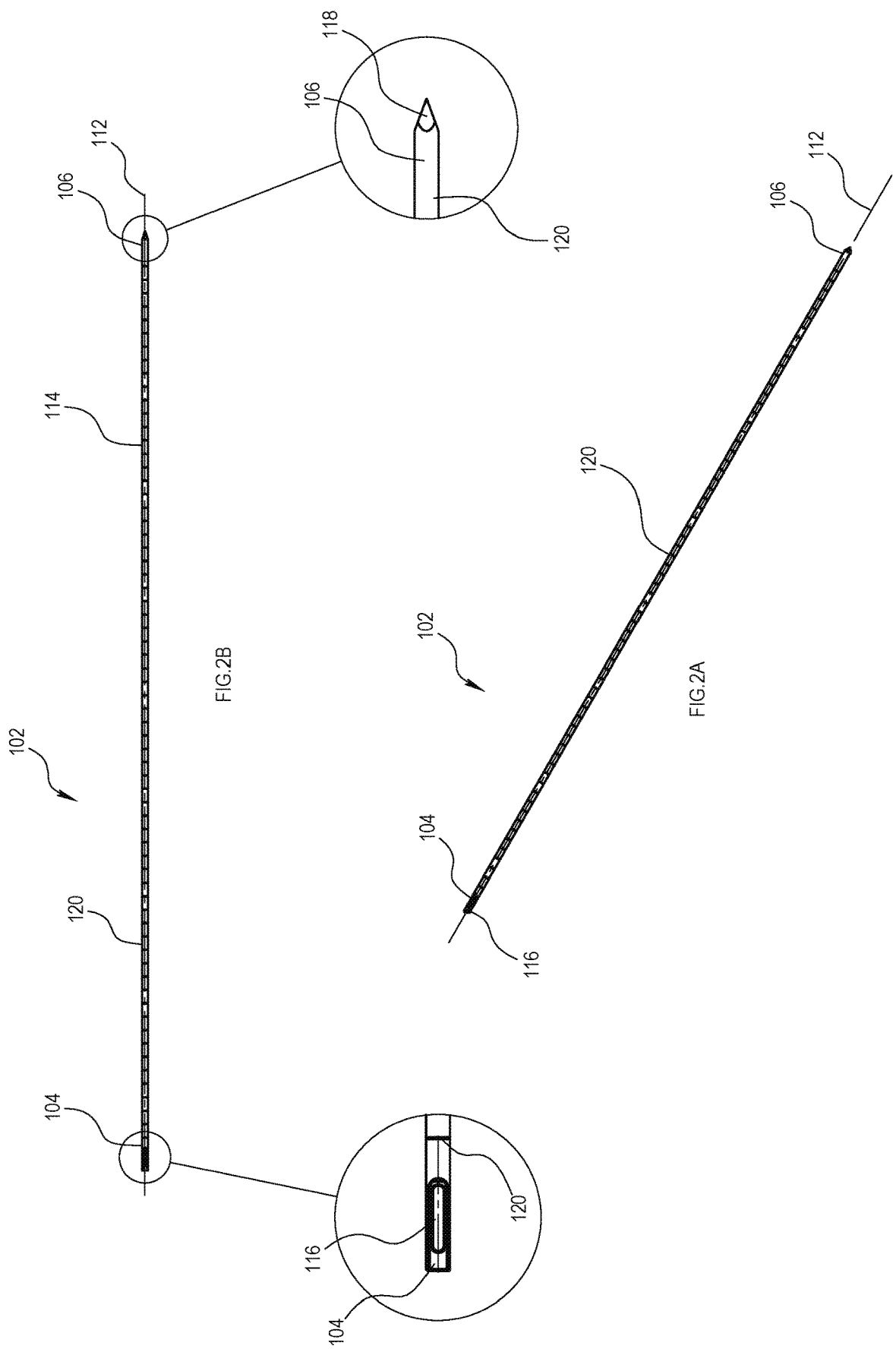

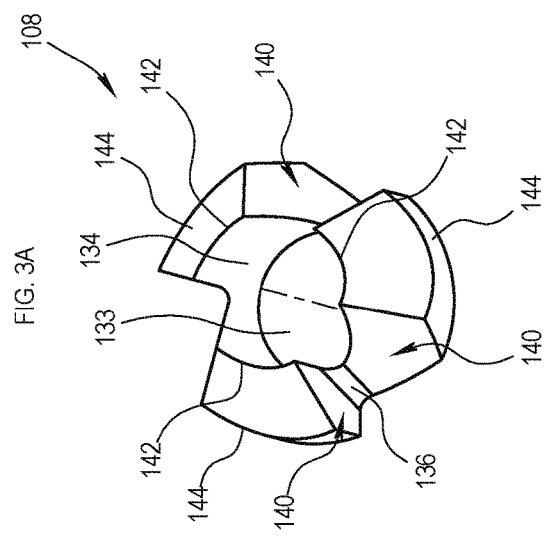
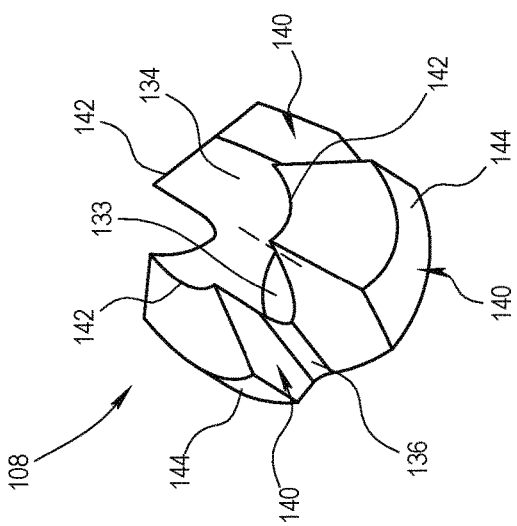
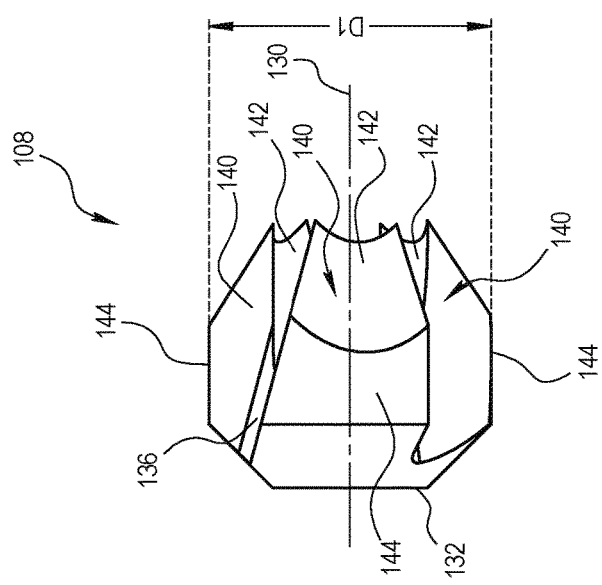
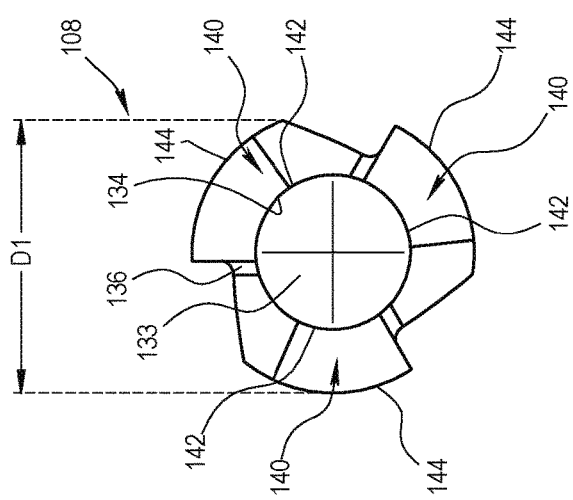

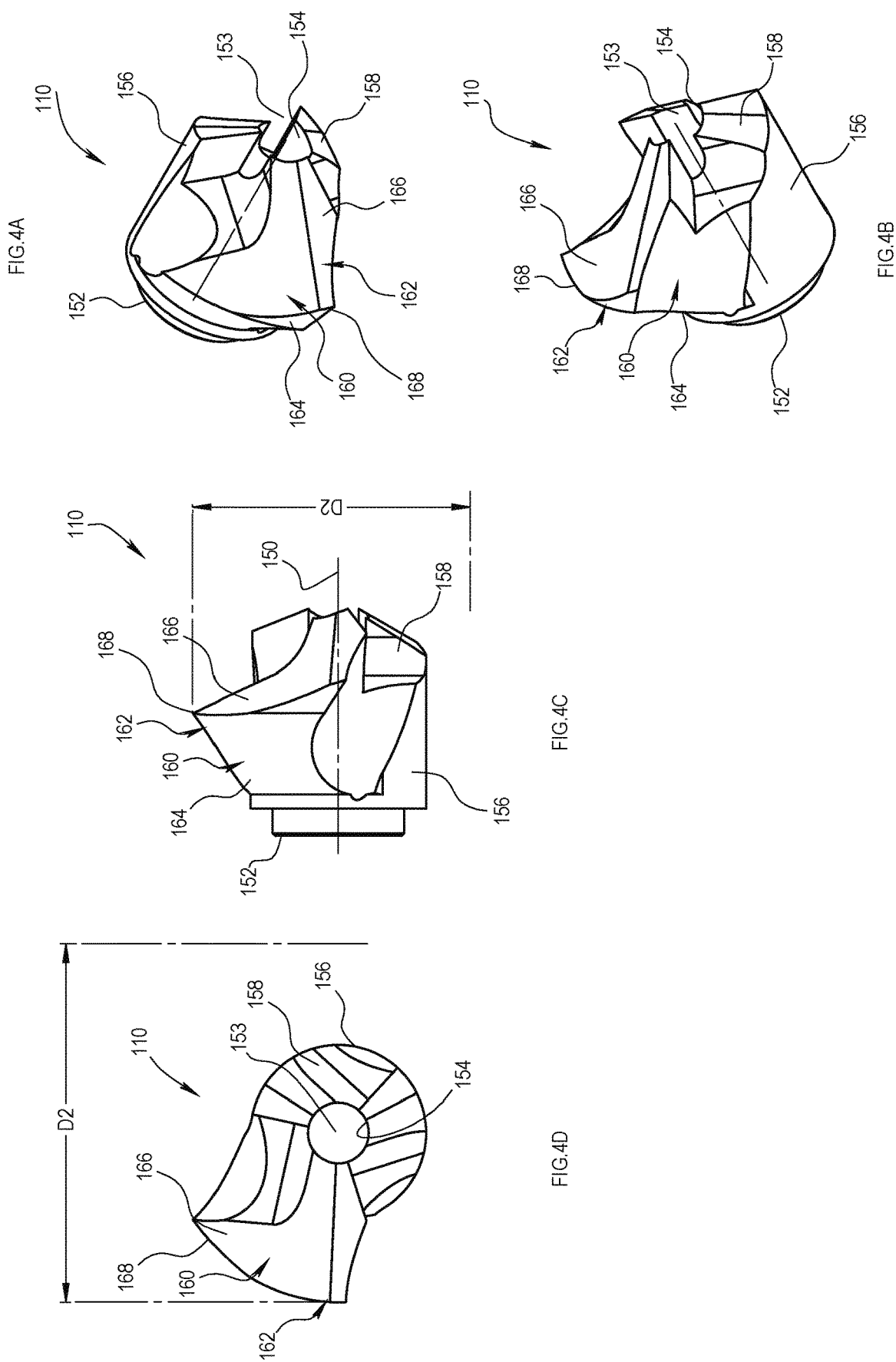

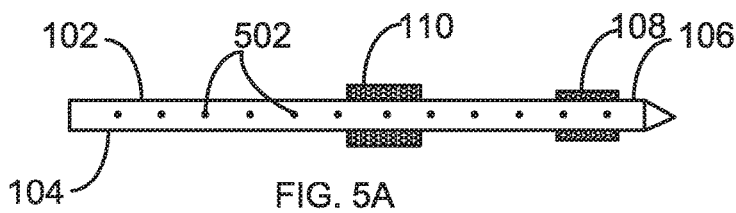
FIG. 5A
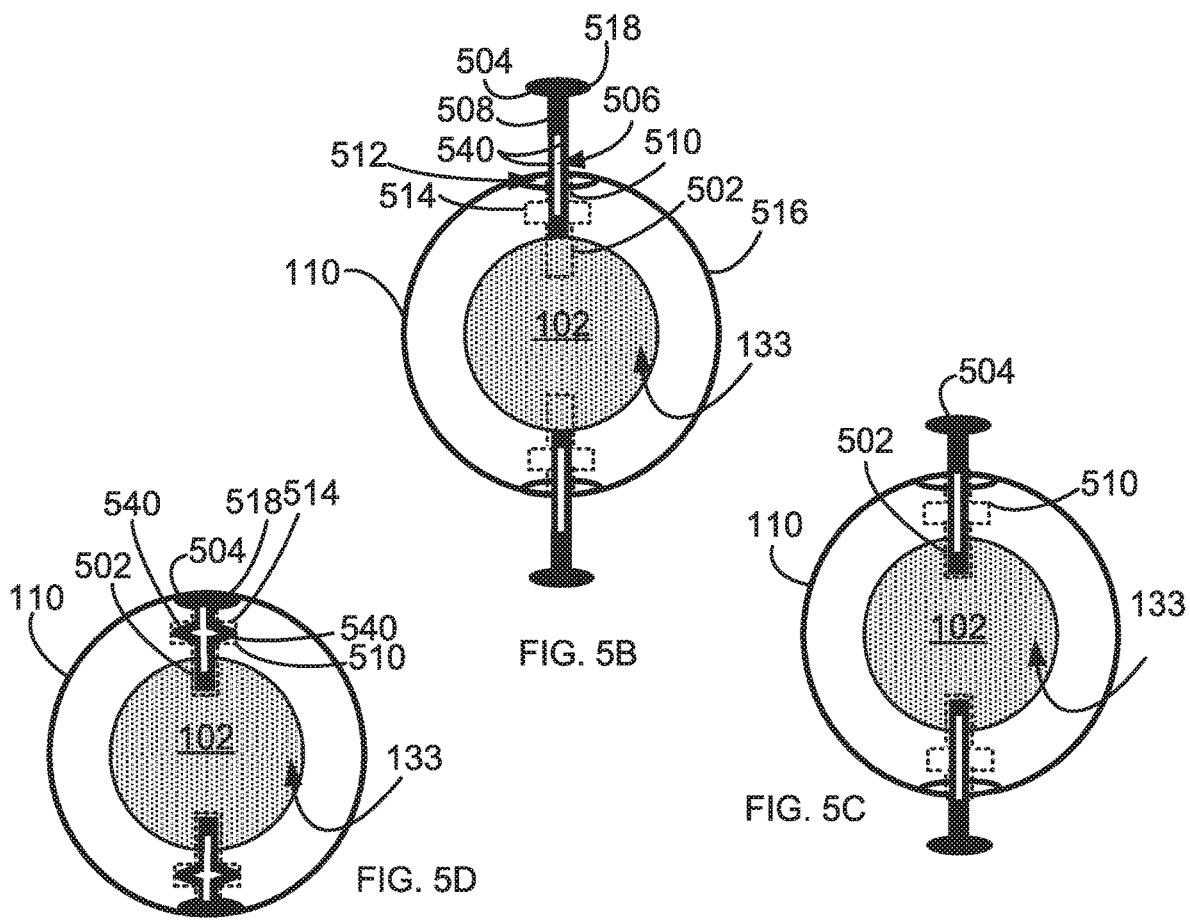
FIG. 5B
FIG. 5C
FIG. 5D
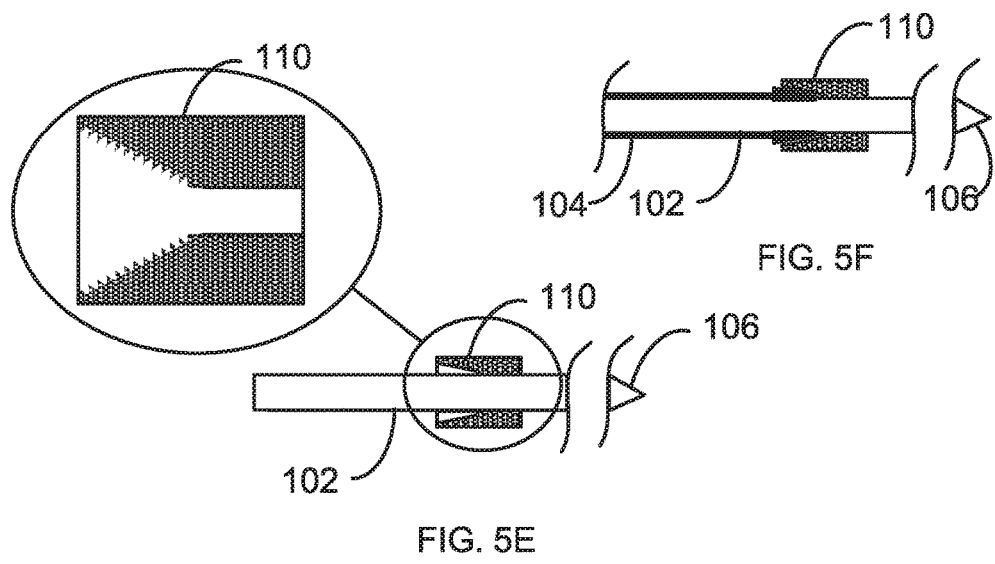
FIG. 5E
FIG. 5F

MULTIPLE HEAD DRILL

RELATED APPLICATIONS

This application is a National Phase of PCT Patent Application No. PCT/IL2017/051053 having International filing date of Sep. 18, 2017, which claims the benefit of priority under 35 USC § 119(e) of U.S. Provisional Patent Application No. 62/396,182 filed on Sep. 18, 2016. The contents of the above applications are all incorporated by reference as if fully set forth herein in their entirety.

FIELD OF THE INVENTION

The present invention generally relates to drilling tools and particularly to tools that change an effective diameter of a bore.

BACKGROUND OF THE INVENTION

It is known that during various arthroscopic procedures drilling of a bore is required within a bone of a patient. In many procedures, the same bore has to have various diameters, such as for insertion of an anchor, administration of a drug, insertion of a graft and insertion of an implant in AVN treatment procedures.

SUMMARY OF THE INVENTION

According to an aspect of some embodiments there is provided drill device, including a shaft having a proximal end and a distal end, at least one first bone cutting head positioned along configured to be positioned along the shaft adjacent the distal end, and at least one second bone cutting head configured to be positioned along the shaft at a location axially proximally spaced from the first bone cutting head. According to some embodiments, at least one of the bone cutting heads is axially positionable along the shaft. According to some embodiments, the bone cutting head comprises a reaming head. According to some embodiments, the bone cutting head comprises a drilling head.

According to some embodiments, the shaft distal end includes a drilling end. According to some embodiments, a diameter, d1 of the first bone cutting head is smaller than a diameter, d2 of the second bone cutting head and the drilling end is configured to drill a bore in bone having the diameter, d1 and a position of the second bone cutting head along the shaft determines a length, L of a portion of the bore having the diameter, d2. According to some embodiments, a distal tip of the shaft is sharp and a distal edge of the drilling head is positioned in continuum with the distal sharp tip to form the shaft drilling end.

According to some embodiments, the tool includes at least one locking mechanism that fixes at least one of the drilling head and the bone cutting head to the shaft. The locking mechanism prevents at least axial movement of the drilling or bone cutting head in respect to the shaft and prevents at least rotation of the drilling or bone cutting head in respect to the shaft. According to some embodiments, a surface of the shaft includes at least one notch, at least one of the drilling or bone cutting heads includes at least one axially oriented hollow and at least one radially oriented through-hole that communicates with the hollow and the locking mechanism includes a slotted fixing pin sized and fitted to be received in the radially oriented through-hole and the notch in the shaft surface. In some embodiments, the bone cutting head comprises a reaming head. In some embodiments, the bone cutting head comprises a drilling head. In some embodiments, a shaft is coupled to two bone cutting heads at least one being a reaming head. In some embodiments, the bone cutting head comprises a drilling head. In some embodiments, a shaft is coupled to two bone cutting heads at least one being a drilling head.

According to some embodiments, the at least one reaming or drilling head includes a threaded proximally facing recess. According to some embodiments, the tool includes a locking cannula threaded into the threaded proximally facing recess, wherein the thread of the threaded proximally facing recess is oriented in a direction opposite to direction of rotation of the reaming head. According to some embodiments, the shaft includes at least one threaded surface segment bordered by a step. According to some embodiments, the reaming head includes an axially oriented hollow defined by a threaded wall and threading the reaming head onto the shaft is limited by the step. According to some embodiments, the thread of the threaded segment is oriented in a direction opposite to direction of rotation of the reaming head.

According to some embodiments, the proximal end of the shaft includes at least one aperture. According to some embodiments, cutting surfaces of the drilling head are oriented in an opposite direction to cutting surfaces of the reaming head. According to some embodiments, the reaming head includes at least one cutting tooth extending radially outwardly.

According to some embodiments, the shaft includes at least one scale mark.

According to an aspect of some embodiments there is provided, a drill device, including a shaft having a proximal end and a distal drilling end and at least one reaming head configured to be moveable along the shaft and fixedly positionable at a location along the shaft.

According to some embodiments, the drilling end drills a bore at a first diameter, d1 and the reaming head expands the bore diameter to a second diameter, d2 and the location along the shaft defines a length of a portion of the bore having a diameter, d2.

According to some embodiments there is provided, a method for drilling a bore in bone, including positioning at least one reaming head along a shaft having a drilling end, drilling a bore in bone having a diameter, d1 and employing the reaming head and expanding the diameter, d1 of the drilled bore to a larger diameter, d2.

According to some embodiments, the positioning includes moving the reaming head to a location along the shaft and fixedly coupling the reaming head to the shaft at the location. According to some embodiments, the fixedly coupling includes threading a locking cannula into a proximally facing recess in the reaming head having a threaded wall. According to some embodiments, the reaming head includes a hollow configured to receive the shaft and the fixedly coupling includes positioning the shaft within the hollow and aligning a radially oriented through hole in the reaming head with a notch on a surface of the shaft and driving a fixing pin through the through hole and the notch.

According to an aspect of some embodiments there is provided a method for preparing a site for implantation of a graft in bone, including measuring a length, L of a graft to be implanted, drilling a bore in bone with a shaft having at least one distal drilling tip, positioning at least one first reaming head on the shaft at a distance from the drilling tip in accordance with the measured length, L and employing the first reaming head and expanding a diameter of the drilled bore to a larger diameter, d2 along a measured distance, L equal to the measured length, L of the graft. According to some embodiments, positioning at least one second reaming adjacent the drilling tip and expanding the drilled bore diameter to a first diameter, d1 smaller than the diameter, d2 reamed by the first reaming head.

According to an aspect of some embodiments there is provided a drill device kit, including a plurality of shafts having each having a proximal end and a distal end, a plurality of reaming heads positioned along at least one first reaming head configured to be positioned along at least one of the shafts adjacent the distal end and at least one second reaming head configured to be positioned along at least one of the shafts at a location axially proximally spaced from the first reaming head. According to some embodiments, at least of the shafts includes at least one scale mark and/or at least of the shafts includes at least one aperture at the proximal end.

According to some embodiments, the plurality of drilling heads and/or reaming heads are of varying diameters. According to some embodiments, the kit includes a dedicated reamer/drilling head fixing tool configured to fix one or more of the drilling and/or reaming heads to one or more of the shafts and/or at least one drilling tool having at least one shaft including at least one integral reaming and/or drilling heads located at a variety of locations along the shaft and having a variety of diameters.

The present invention seeks to provide a multi-headed drill. There is thus provided in accordance with an embodiment of the present invention a drill device, including a longitudinal shaft having a proximal end and a distal drilling end, a first reaming head positioned along the longitudinal shaft and disposed adjacent the distal drilling end and a second reaming head adapted to be positioned along the longitudinal shaft at a location longitudinally spaced from the first reaming head.

Preferably, the first reaming head has at least one cutting tooth defining a first diameter. Further preferably, the second reaming head has at least one cutting tooth defining a second diameter. Still further preferably, the second diameter is greater than the first diameter.

In accordance with an embodiment of the present invention, the longitudinal shaft is made of Nitinol.

Preferably, the second reaming head is adapted to be positioned along the longitudinal shaft through the proximal end thereof. Alternatively, the second reaming head is adapted to be positioned along the longitudinal shaft from the side of the shaft.

In accordance with an alternative embodiment of the present invention, a drill device, including a longitudinal shaft having a proximal end and a distal drilling end, a first reaming head positioned along the longitudinal shaft and disposed adjacent the distal drilling end and a second reaming head fixedly attached to the longitudinal shaft at a distance from the first reaming head.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The present invention will be understood and appreciated more fully from the following detailed description, taken in conjunction with the drawings in which:

FIGS. 1A, 1B, 1C, 1D, 1E, 1F and 1G are perspective view and side view simplified illustrations of a fully assembled Multiple Headed Drill in accordance with some embodiments of the present invention;

FIGS. 2A and 2B are perspective view and side view simplified illustrations of a shaft of a Multiple Headed Drill in accordance with some embodiments of the invention and;

FIGS. 3A, 3B, 3C and 3D are perspective views taken from different directions, side view and top view simplified illustrations of a reaming head of a Multiple Headed Drill and in accordance with some embodiments of the invention;

FIGS. 4A, 4B, 4C and 4D are perspective views taken from different directions, side view and top view of a reaming head of a Multiple Headed Drill and in accordance with some embodiments of the invention;

FIGS. 5A, 5B, 5C, 5D, 5E, 5F, 5G, 5H and 5I are side view and cross-section view simplified illustrations of locking mechanisms of a reamer or drilling head to a shaft;

DESCRIPTION OF SPECIFIC EMBODIMENTS OF THE INVENTION

Figure 1A:
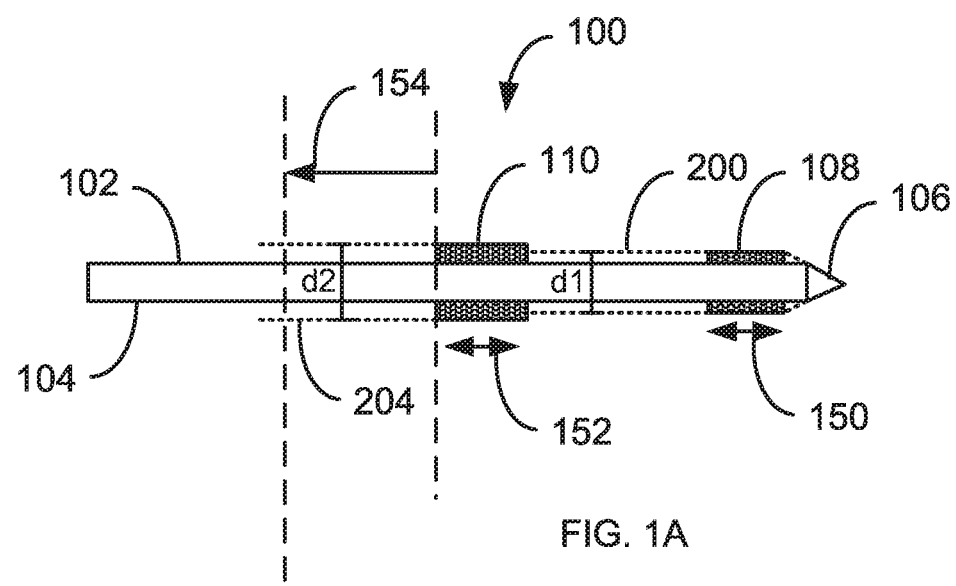

The present invention generally relates to drilling tools and particularly to tools that change an effective diameter of a bore.

An aspect of some embodiments of the invention relates to a bone drilling tool comprising a shaft having drilling end and one or more reaming heads positioned on the shaft. In some embodiments, the one or more reaming heads are positionable along the shaft at varying distances from the distal end. In some embodiments, at least one of the reaming heads is configured to widen a drilled bore to a diameter sized and fitted to receive an implant.

An aspect of some embodiments of the invention relates to a bone drilling tool. In some embodiments, the bone drilling tool comprises a shaft and one or more drilling heads and one or more reaming heads positioned on the same shaft. In some embodiments, the drilling heads and reaming heads are positioned separately on the shaft. In some embodiments, the drilling heads and reaming heads are positioned concurrently on the same shaft.

In some embodiments, one or more drilling heads and reaming heads are positioned to the same shaft at different locations on the shaft. In some embodiments, one or more of the shafts comprises a proximal aperture.

In some embodiments, one or more of the drilling heads and/or reaming heads comprises an axially oriented hollow. In some embodiments, the hollow is centrally located. In some embodiments, the one or more of the drilling heads and/or reaming heads comprises a central hollow having a circumferential gap in a wall forming a C-shaped cross-section.

In some embodiments, the bone drilling tool comprises a pointed shaft and one or more drilling heads positioned adjacent to the pointed shaft. In some embodiments, the shaft comprises a drilling end. In some embodiments, the shaft comprises one or more scale marks. In some embodiments, at least one of the drilling head and reaming head is positioned on the shaft in accordance with one or more of the scale marks.

An aspect of some embodiments of the invention relates to a bone drilling tool comprising at least one locking mechanism configured to lock at least one reaming head and drilling head to the bone drilling tool shaft. In some embodiments, the lock prevents axial movement of the head in respect to the shaft. In some embodiments, the lock prevents rotational movement of the head in respect to the shaft. In some embodiments, a locking mechanism comprises a locking proximal cannula. In some embodiments, the mechanism comprises a slotted fixing pin. In some embodiments, the locking mechanism comprises threading a reamer or drilling head onto a threaded segment of a bone drilling tool shaft.

An aspect of some embodiments of the invention relates to a bone drilling tool kit. In some embodiments, the bone drilling tool kit comprises one or more shafts having a pointed tip. In some embodiments, the kit comprises one or more shafts having a drilling tip. In some embodiments, the shafts are in varying diameters. In some embodiments, one or more shafts comprise scale marks. In some embodiments, one or more of the shafts comprises a proximal aperture.

In some embodiments, the kit comprises one or more drilling heads. In some embodiments, the kit comprises one or more reaming heads. In some embodiments, one or more of the drilling heads and/or reaming heads are in varying diameters. In some embodiments, one or more of the drilling heads and/or reaming heads comprise different locking systems.

An aspect of some embodiments of the invention relates to a method of using a bone drilling tool in preparation of a site in bone for implantation of a graft. In some embodiments, the method comprises measuring a length, L of a graft to be implanted. In some embodiments, the method comprises providing a shaft having a distal drilling tip and one or more scale marks. In some embodiments, the method comprises drilling a bore in the bone to a desired depth. In some embodiments, the method comprises mounting at least one reaming head on the shaft at a level of an entry hole in the surface of the bone.

In some embodiments, the method comprises measuring a distance, d proximally on the shaft from the surface entry hole of the drilling tool that corresponds to the measured graft length, L an identified by a scale mark on the shaft and continuing drilling to a point at which the identified scale mark reaches the entry hole in the surface of the bone indicating a second depth equal to the distance, d.

In some embodiments, the method comprises drilling a bore to a point until the drilling tip of the shaft forms an exit hole in a surface of the bone. In some embodiments, the reaming head is positioned along the shaft so that a distal surface of the reaming head is disposed against the surface of the bone. The method comprises continuing to drill through the bone until the scale mark indicates that a distance from the drilling tip to the exit hole of the drilling tool is distance, d.

In some embodiments and optionally, the shaft comprises a pointed tip and the method comprises mounting a drilling head onto the distal end of the shaft. In some embodiments, the drilling head is mounted in continuum with the distal sharp end to form a shaft drilling tip.

A bone material removal device is disclosed herein, which is particularly useful for drilling a bore with varying diameters within a bone of a patient using a single drilling tool. In some embodiments, the tool is configured to be disposable.

The term "Double Headed Drill" as used herein refers to a drilling tool comprising one or more drilling heads and/or reaming heads configured to be mounted concurrently or separately on the same shaft.

The term "Head" as used herein relates to separate bone cutting piece associated with a shaft and used to drill or expand a bore in a bone.

The term "Drilling Head" as used herein refers to a bone cutting head, a distal end of which tapers to diameter of zero ($\Phi=0$).

The term "Reaming Head" as used herein refers to a bone cutting head, a distal end of which tapers to a diameter of the shaft of the bone drilling tool.

Reference is now made to FIGS. 1A, 1B, 1C, 1D, 1E, 1F and 1G, which are plan view and perspective view simplified illustrations of a Multiple Headed Drill, constructed and operative in accordance with exemplary embodiments of the present invention.

Figure 1B:
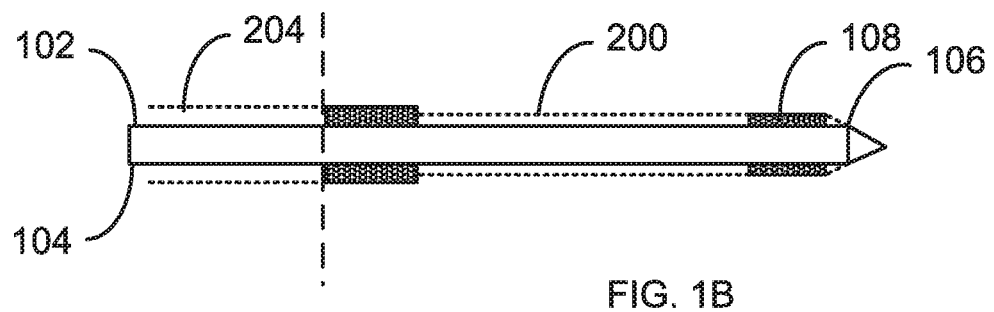

FIG. 1A depicts an exemplary embodiment of a bone drilling tool 100 comprising a shaft 102 having a sharp distal end 106 and a proximal end 104 coupleable to a handle or a power tool. In the embodiment shown in FIG. 1A tool 100 comprises one or more distal reamers 108 and proximal reamers 110 placed on shaft 102. One or both reamers 108/110 are positionable at a desired location along shaft 102 as depicted by double headed arrows 150 and 152. In some embodiments, the positions are continuous. In some embodiments, the positions are analogous (e.g., marks 120 or notches 502). In some embodiments, one or both reamers 108/110 are positionable between 10 and 60 mm along shaft 102. In some embodiments, one or both reamers 108/110 are positionable between 20 and 50 mm along shaft 102. In some embodiments, one or both reamers 108/110 are positionable between 30 and 40 mm along shaft 102. In some embodiments, one or both reamers 108/110 are positionable less than 10, more than 60 mm or any fraction in between along shaft 102. FIG. 1B illustrates the same tool 100 depicted in FIG. 1A, in which reaming head 110 has been positioned at a more proximally position than the position of reaming head 110 in FIG. 1A as indicated by arrow 154. In the configuration shown in FIG. 1B, the position of reaming head 108 has not changed.

Figure 1C:
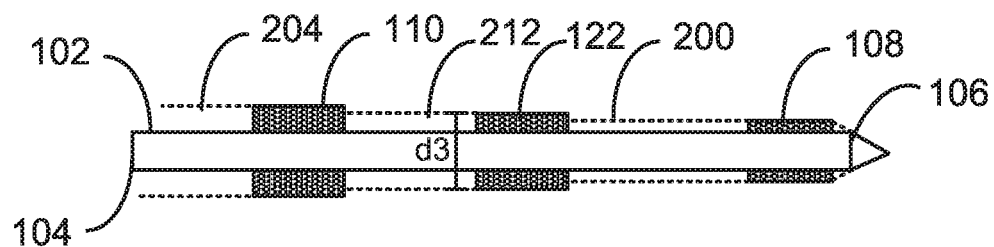

The exemplary embodiment depicted in FIG. 1C illustrates a configuration of tool 100 comprising three reaming heads 108/110 and 122. In the example shown in FIG. 1C, reaming head 122 is positioned between reaming heads 108 and 110 and has an intermediate diameter smaller than the diameter of proximal head 110 and larger than the diameter of distal head 108. Reaming head 122 is configured to expand a drilled bore e.g., bore 200 to a bore 212 having an intermediate diameter (d3).

Figure 1D:
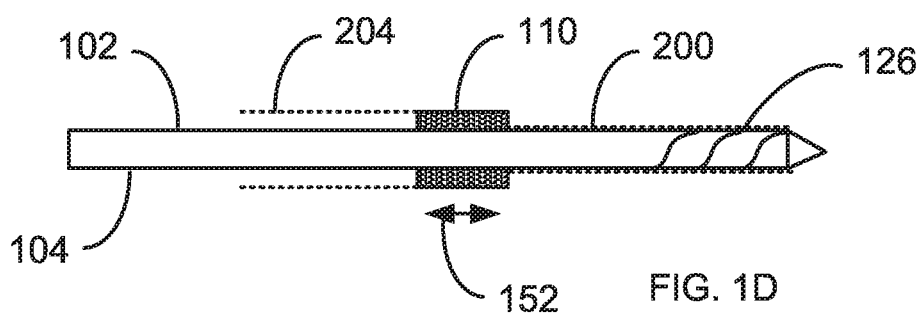
Figure 1E:
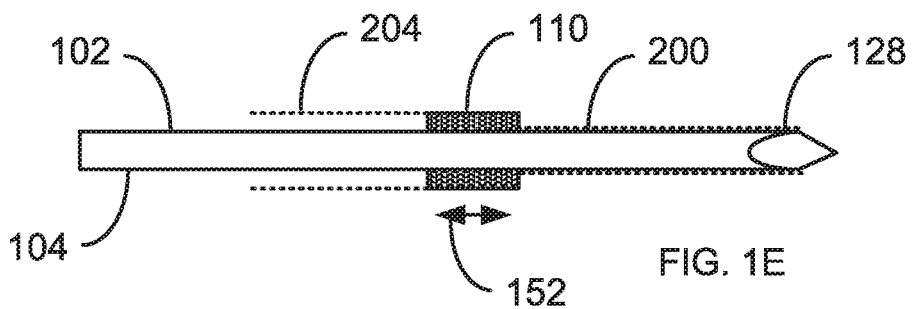

FIGS. 1D and 1E illustrate tools 100 comprising drilling distal ends 126 and 128. In the exemplary embodiment shown in FIG. 1D, shaft 102 comprises a fluted distal drilling end 126. FIG. 1E depicts an exemplary embodiment in which shaft 102 comprises a diamond tip distal drilling end 128. In some embodiments, shaft 102 comprises a coned sharp tip or a trocar-type drilling tip.

In some embodiments, optionally and alternatively and as explained elsewhere herein, distal reaming head 108 comprises a bone cutting head configured to drill an initial bore 200 at a diameter, d1. In some embodiments, a diameter of reaming head 110 is larger than a diameter of reaming head 108 and is configured to expand bore 200. Reaming head 110 expands the diameter of bore 200 along a segment 204 from a diameter, d1 to a larger diameter, d2.

Figure 9:
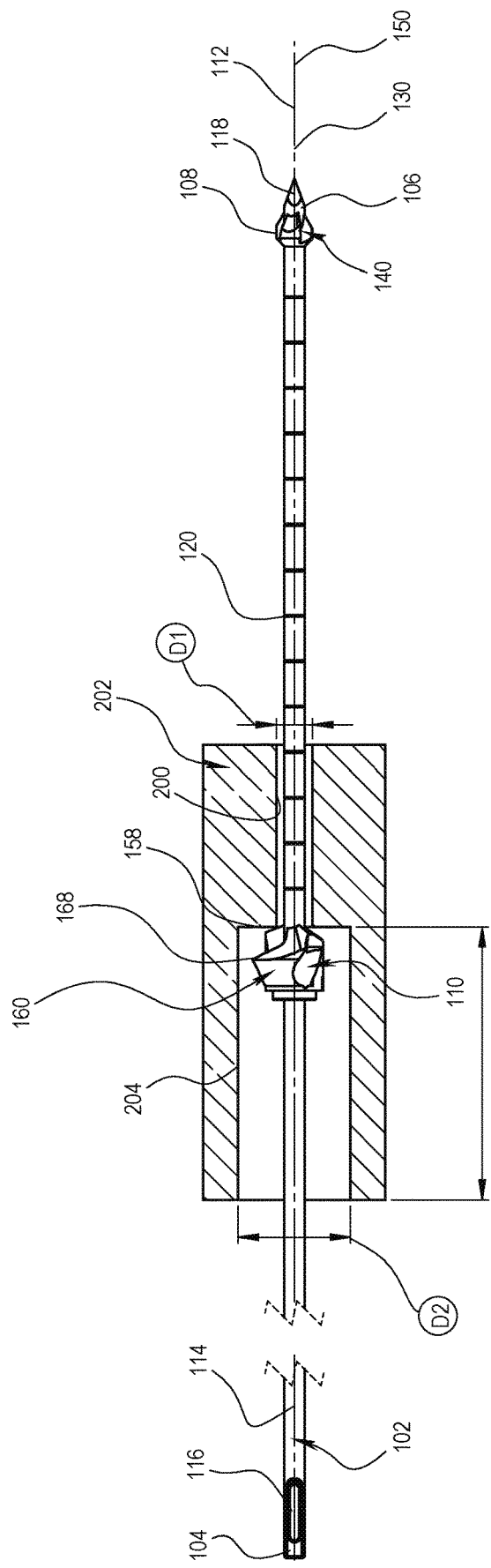
FIG. 9 is a simplified illustration of a fourth operative stage of a Multiple Headed Drill, in accordance with some embodiments of the invention.

Along a segment 204 of bore 200 having a length, L (FIG. 9).

It is seen in FIGS. 1F and 1G that double head drill 100 preferably comprises a longitudinal leading shaft 102 having a proximal end 104 and a distal end 106. In some embodiments and optionally, distal end 106 comprises a pointed tip. In some embodiments, distal end 106 comprises a fluted drilling tip. In the exemplary embodiment shown in FIGS. 1A and 1B, a drilling head 108 attached to longitudinal shaft 102 and a reaming head 110, which is adapted to be positioned along longitudinal shaft 102. In some embodiments and optionally, drilling head 108 is replaced with a reaming head. It is appreciated that double head drill 100 is adapted for connection with a power tool for drilling a varying diameter bore within a bone of a patient for insertion of a graft therewithin.

The selection of the number of drilling/reaming heads and their position on shaft 102 depends on the procedure and type of shaft to be used. In some procedures, tool 100 comprises a resilient or semi-resilient shaft 102, which limits the diameter (e.g., less than or equal to 4 mm) of a shaft that can be used. In such a case, a distal reaming head 108 is positioned on a distal end 106 of shaft 102 to expand a first bore 200 drilled by a drilling tip of shaft 102 to a diameter, d1. In some embodiments, a resilient or semi-resilient shaft 102 can be provided with an integrally formed distal reaming head 108.

In procedures in which shaft 102 can be more rigid, a larger diameter (e.g., greater than 4 mm) drilling shaft can be selected negating the need for a distal reaming head 108 and a distal reaming head may be used or not.

A potential advantage of a double-headed drilling tool is in that a single tool is used during an entire operative procedure, which is configured, for example, to enable creation of a socket for placement of a graft.

Reference is now made to FIGS. 2A and 2B, which are perspective view and side plan view simplified illustrations of shaft 102, forming part of the Multiple Headed Drill 100 of FIGS. 1F and 1G.

In some embodiments, longitudinal shaft 102 preferably comprises an integrally formed element having a longitudinal axis 112 and optionally made of a resilient material such as, for example, Nitinol, thus providing resiliency characteristics to the shaft 102. Shaft 102 defines an outer surface 114. In some embodiments and optionally, an aperture 116 is formed generally at the proximal end 104 of shaft 102.

It is also seen that shaft 102 has a sharp tip 118 formed at the distal end 106 thereof. In some embodiments and optionally, distal end 106 comprises a fluted drilling tip.

It is additionally seen, in some embodiments, that a plurality of scale marks 120 are provided along at least a portion of the outer surface 114 of shaft 102, for example, to indicate the drilling depth for the physician.

Reference is now made to FIGS. 3A-3D, which are perspective view (of different aspects taken from different directions), side plan view and top plan view simplified illustrations of the first reaming head 108, forming part of the Multiple Headed Drill 100 of FIGS. 1F and 1G. In some embodiments and optionally, head 108 comprises a drilling head.

It is seen in the exemplary embodiment depicted in FIGS. 3A-3D that first reaming head 108 is an integrally formed element arranged along longitudinal axis 130 and is preferably made of a suitable bio-compatible material, e.g., a metal.

In some embodiments, first reaming head 108 comprises a generally hollow cylindrical element having a proximal edge 132, an axially oriented central bore or hollow 133 defining a generally circular inner surface 134, and an outer surface 136. In some embodiments, a plurality of mutually azimuthally spaced cutting teeth 140 are formed on outer surface 136 and preferably extend radially outwardly from outer surface 136 and distally from proximal edge 132. Each of the cutting teeth 140 define a distalmost cutting edge 142 and an outer surface 144, forming part of a circumferential outer surface of an imaginary cylinder formed by cutting teeth 140 and having a diameter D1, defining the resulting diameter of the bore drilled in the bone of the patient by cutting tooth 140.

It is appreciated that a single or any number of cutting teeth 140 can be formed on the outer surface 136 of first reaming head 108, cutting teeth can have any geometrical shape and be mutually azimuthally spaced from each other by any angle.

In some embodiments and optionally, reaming or drilling head 108 may include a gapped wall (not shown) between inner surface 134 and outer surface 136 forming a C-shaped cross-section for optionally mounting reaming or drilling head 108 sideways (e.g., snap-fit) onto shaft 102.

Reference is now made to FIGS. 4A-4D, which are perspective view (of different aspects taken from different directions), side plan view and top plan view simplified illustrations of the second reaming head 110, forming part of the Multiple Headed Drill 100 of FIGS. 1F and 1G.

It is seen in the exemplary embodiment depicted in FIGS. 4A-4D that second reaming head 110 is an integrally formed element arranged along longitudinal axis 150 and is preferably made of Nitinol or any other suitable bio-compatible metal.

In some embodiments, second reaming head 110 comprises a generally hollow cylindrical element having a proximal edge 152, a central bore 153 defining a generally circular inner surface 154, and an outer surface 156. In some embodiments, a plurality of cutting edges 158 are formed on a distal end of second reaming head 110. A cutting tooth 160 is formed on outer surface 156 and preferably extend radially outwardly from outer surface 156 and distally from proximal edge 152. The cutting tooth 160 preferably has an outer surface 162, which defines the resulting diameter of the bore drilled in a bone of the patient. It is appreciated that in this particular embodiment of the present invention, cutting tooth 160 defines a distally extending radially outwardly tapered outer surface 164 and a distally extending radially inwardly tapered outer surface 166 joined by a partially circumferential edge 168, defining the largest distance with respect to longitudinal axis 150, thus defining the resulting diameter D2 of the bore drilled in the bone of the patient by cutting tooth 160.

It is appreciated that any number of cutting teeth 160 can be formed on the outer surface 156 of second reaming head 108, cutting teeth can have any geometrical shape and be mutually azimuthally spaced from each other by any angle.

In some embodiments and optionally, reaming head 110 may include a gapped wall (not shown) between inner surface 154 and outer surface 156 forming a C-shaped cross-section for optionally mounting reaming or drilling head 110 sideways (e.g., snap-fit) onto shaft 102.

Reference is now made to FIGS. 5A, 5B, 5C, 5D, 5E, 5F, 5G, 5H and 5I, which are plan view and cross-sectional view simplified illustrations of locking mechanisms of drilling heads 108 and/or reaming heads 110 to shaft 102 in accordance with some embodiments of the invention. As described elsewhere herein, location of drilling heads 108 and/or reaming heads 110 is adjustable along shaft 102 e.g., to adjust for a measured length, L of an implant to be introduced into a drilled bore in bone.

In some embodiments, drilling heads 108 and/or reaming heads 110 comprise one or more locking mechanisms that prevent axial movement of the heads in respect to the shaft 102 and fix drilling heads 108 and/or reaming heads 110 to shaft 102 in a selected axial position in respect to distal end 106 and/or prevent drilling heads 108 and/or reaming heads 110 from rotating in respect to shaft 102. In some embodiments and as shown in FIG. 5A, shaft 102 comprises one or more notches 502 sized and fitted to receive drilling heads 108 and/or reaming heads 110 location fixing pins 504. In some embodiments, notches 502 are distributed along a surface of shaft 102, axially and in parallel to a longitudinal axis of shaft 102. In some embodiments, notches 502 are distributed along one side of shaft 102. In some embodiments, notches 502 are distributed along both sides of shaft 102 and in some embodiments, notches 502 are distributed spirally about the longitudinal axis of shaft 102.

FIGS. 5B, 5C and 5D illustrate a cross section view of a reaming head 110 and shaft 102 at a level of a notch 502 in accordance with an embodiment of the invention. As shown in the exemplary embodiment in FIGS. 5B and 5C, reaming head 110 comprises a hollow 133 configured to receive shaft 102 and shaft 102 is positioned within hollow 133. In some embodiments, reaming head 110 comprises a radially oriented through hole 510 having a cross-shaped cross-section and sized and fitted to receive a slotted fixing pin 504. In some embodiments, radially oriented through hole 510 communicates with a hollow 133 in reaming head 110. In some embodiments, through hole 502 opens peripherally to a recess 512 in the surface 516 of reaming head 110 sized and shaped to receive a head 518 of slotted fixing pin 504.

In some embodiments, fixing pin 504 comprises a slot 506 in a stem 508 that forms bendable partial prongs 540 in stem 508. FIG. 5B depicts reaming head 110 positioned on shaft 102 with radially oriented through hole 510 aligned with a notches 502. In the embodiment shown in FIGS. 5B-5D, shaft 102 comprises diametrically opposed notches 502, however and as described elsewhere herein, in some embodiments, shaft 102 may comprise notches 502 on one side only of shaft 102. FIG. 5C depicts fixing pin 504 driven further to a point at which fixing pin 504 cannot be driven radially inwards any further at which point, and as shown in FIG. 5D, partial prongs 540 formed by slot 506 bend into arms 514 of cross-shaped through hole 502, placing pin 504 head 518 into recess 512. In some embodiments, a dedicated reamer/drilling head fixing tool (e.g. a crimping tool) can be used to drive fixing pin radially inwards and lock reamer head 110 onto shaft 102.

In some embodiments, drilling tool 100 comprises a locking cannula 520 operative to lock reaming head 110 into position and prevent it from rotating in respect to shaft 102. In some embodiments, reaming head 110 comprises a proximally facing recess, at least a part of which comprises a locking cannula coupling portion 522. In some embodiments, coupling 522 is cone shaped. In some embodiments, coupling portion 522 comprises a threaded wall 524. In some embodiments, locking cannula 520 comprises a distal coupling portion 526 threaded and sized and shaped to be threaded and received inside locking cannula coupling portion 522 as shown in FIG. 5F. In some embodiments, a proximal end of locking cannula 520 is coupled to a handle or shaft rotation driving tool preventing axially proximally movement of locking cannula 520. In some embodiments, the orientation of the thread of threaded wall 524 is opposite to the direction of rotation of reaming head 110. Other locking mechanisms can be used for example, a pin-in-groove locking system or a clamp locking system.

Figure 5G:
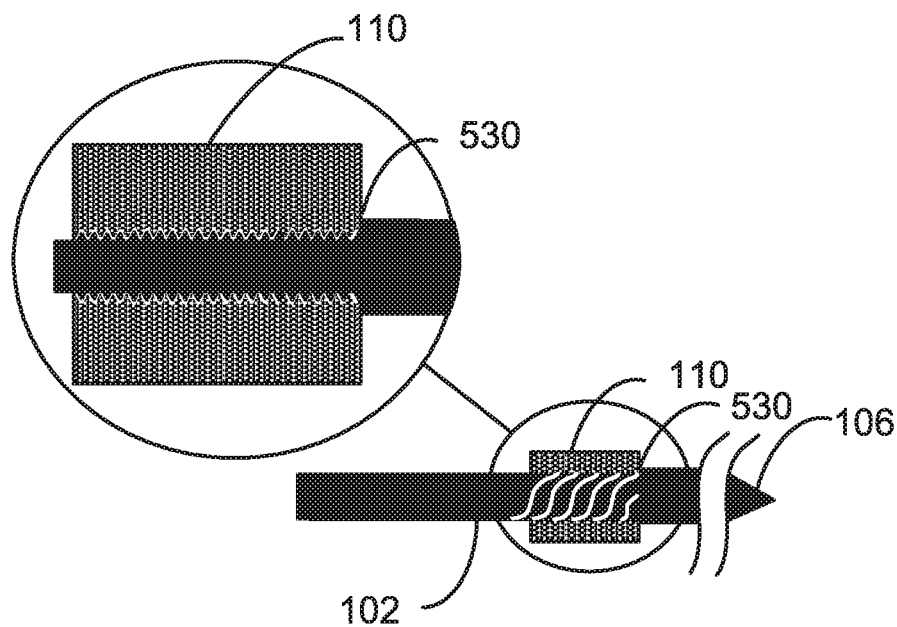
Figure 5H:
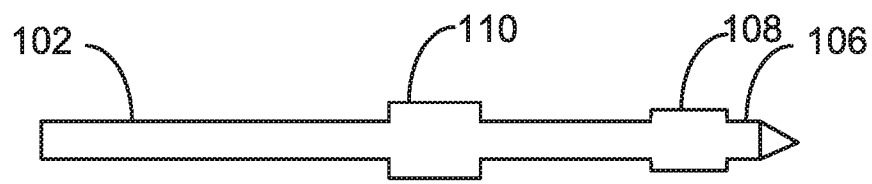
Figure 5I:
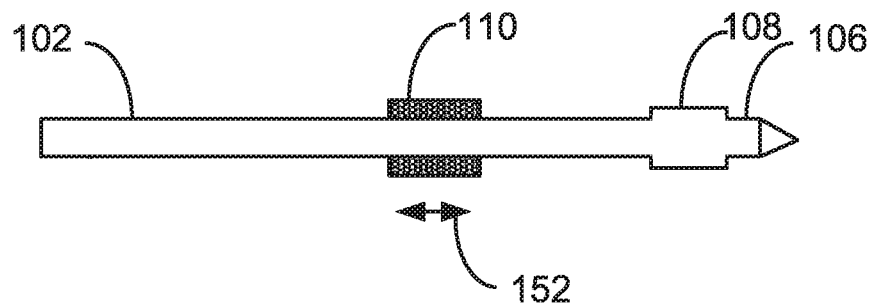

FIG. 5G depicts an exemplary embodiment in which reaming head 110 comprises an axially oriented hollow defined by a threaded wall. In some embodiments, shaft 102 comprises a threaded segment 528 bordered proximally or distally by a step 530 on the surface of shaft 102. In the embodiment in FIG. 5G, step 532 is positioned distally to reamer head 110 which is positioned along shaft 102 and threaded onto threaded segment 528 until stopped at step 532. In some embodiments, the orientation of the thread of threaded segment 532 is opposite to the direction of rotation of reaming head 110. In some embodiments and as illustrated in the exemplary embodiment depicted in FIG. 5H, shaft 102 and one or more reaming heads 108/110 are formed integrally as a single integral unit. Alternatively and optionally and as shown in FIG. 5I, in some embodiments, drilling or reaming head 108 is formed integrally with shaft 102 as a single integral unit and reaming head 110 is positionable as explained elsewhere herein.

As described elsewhere herein, in some embodiments shaft 102 comprises a sharp tip and in some embodiments shaft 102 comprises a drilling tip. In instances in which shaft 102 comprises a sharp tip, a drilling head 108 is selected to drill the initial bore. In such a configuration, drilling tip 108 is positioned along the distal end of shaft 102 in continuum with sharp or pointed tip 118 to avoid a stepped drilling end and form a drilling end having a continuous tapering surface. In instances in which shaft 102 comprises a drilling end, a reaming head 108 is selected to widen a previously drilled bore to a first diameter.

Figure 6:
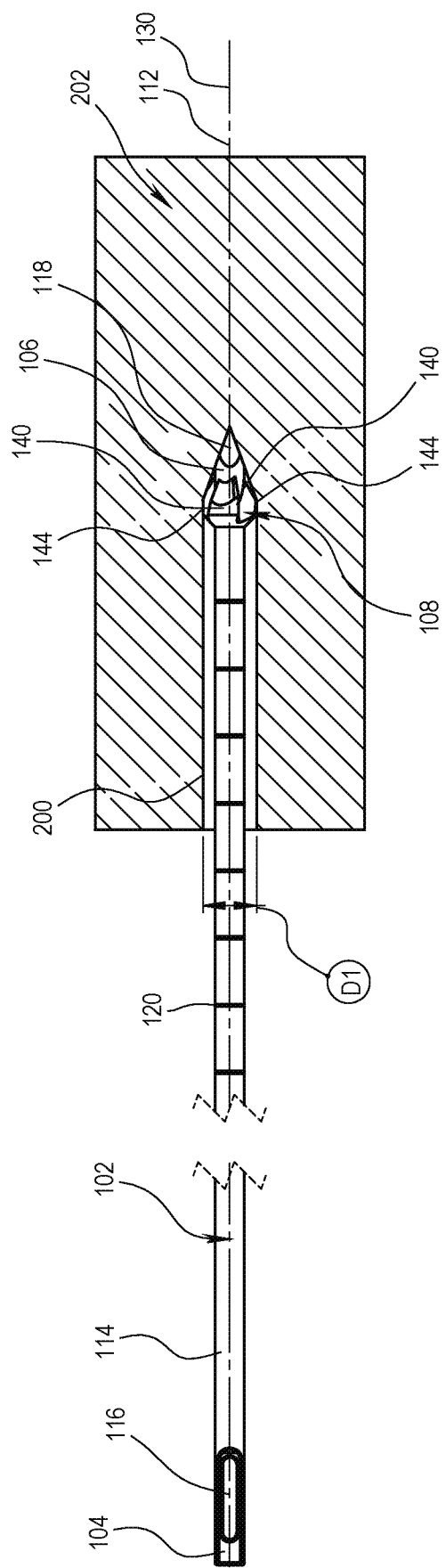
FIG. 6 is a simplified illustration of a first operative stage of a Multiple Headed Drill, in accordance with some embodiments of the invention positioned along.

Reference is now made to FIG. 6, which is a simplified illustration of an example of a first operative stage of the Multiple Headed Drill 100, showing only the drilling head 108 positioned along the shaft 102 during initial stage of drilling a bore in the bone of the patient.

It is seen in the exemplary embodiment depicted in FIG. 6 that the Multiple Headed Drill 100 having only the drilling head 108 mounted thereon, such that longitudinal axes 112 and 130 are aligned, forming a first bore 200 within bone 202 of the patient, upon initial advancement of the Multiple Headed Drill 100 into bone 202.

It is a particular feature of an embodiment of the present invention that drilling head 108 is mounted in closed proximity to or in continuum with sharp tip 118 of shaft 102. It is appreciated that the sharp tip 118 of shaft 112 is adapted to lead the drilling procedure, while the drilling head 108 disposed slightly proximally thereof, is adapted to define the first bore 200, having a diameter D1, formed by outer surfaces 144 of cutting teeth 140 of drilling head 108 during initial advancement of the Multiple Headed Drill 100 into the bone 202 using a power tool.

Alternatively and optionally and as disclosed elsewhere herein, in some embodiments, shaft 102 includes a drilling end in which case one or more reaming heads are mounted on shaft 102 to produce a bore having varying diameters.

It is a particular feature of an embodiment of the present invention that sharp tip 118 of shaft 102 guides the drilling procedure, it provides direction of drilling to shaft 102 and keeps the shaft 102 in a straight orientation, it also guides drill head 108.

It is noted that the scale marks 120 provided on outer surface 114 of shaft 102 enable the physician to obtain an indication of the depth of the resulting drilled bore 200. In some embodiments, the scale marks 120 provide an indication for positioning a drilling or reaming head, a measured depth of a drilled bore or a length of a bore segment to be reamed and expanded.

Figure 7:
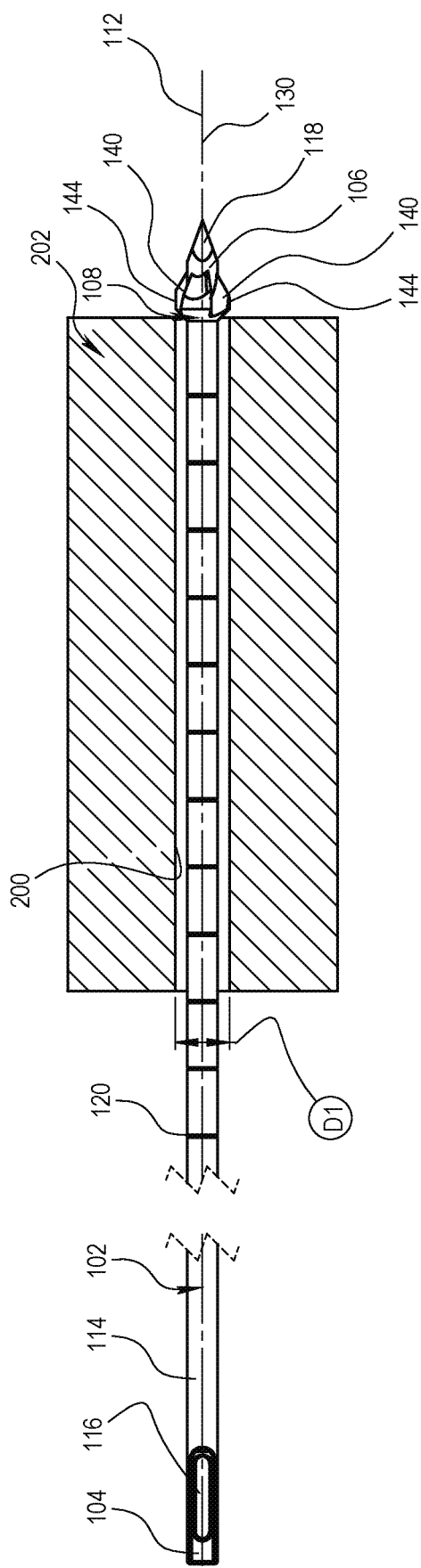
FIG. 7 is a simplified illustration of a second operative stage of a Multiple Headed Drill, in accordance with some embodiments of the invention positioned along.

Reference is now made to FIG. 7, which is a simplified illustration of an example of a second operative stage of the Multiple Headed Drill 100, still showing only the drilling head 108 positioned along the shaft 102 during complete insertion into bone 202 of a patient.

Figure 8:
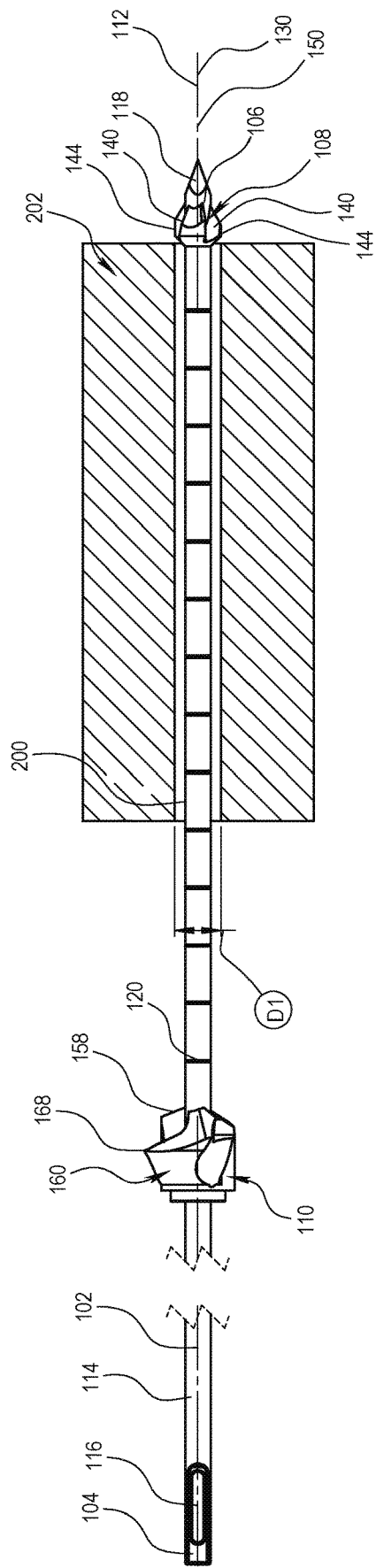
FIG. 8 is a simplified illustration of a third operative stage of a Multiple Headed Drill, in accordance with some embodiments of the invention.

It is seen in the example in FIG. 7 that the Multiple Headed Drill 101 having the drilling head 108 mounted thereon is advanced through the bone 202 of the patient. Physician receives an indication of drill passage through the entire bone by means of scale marks 120 provided on the outer surface 114 of shaft 102. Reference is now made to FIG. 8, which is a simplified illustration of a third operative stage of the Multiple Headed Drill 100, showing the mounting of the second reaming head 110 onto the shaft 102, which is inserted into the bone 202 of the patient.

It is seen in FIG. 8 that the second reaming head 110 is now also positioned along shaft 102, such that longitudinal axes 112, 130 and 150 are aligned.

It is a particular feature of an embodiment of the present invention that the second reaming head 110 is positioned along shaft 102. Second reaming head 110 is configured to form an enlarged bore portion within the bone 202 of the patient, sized to fit a graft inserted thereto during the surgical procedure.

In an embodiment of the present invention where the second reaming head 110 is positioned along shaft 102 during the surgical procedure, the drilled bore geometry is not pre-defined and can be adjusted in accordance to the preferences of the physician, who can mount the second reaming head 110 at any location along shaft 102 chosen by the physician using the provided scale marks 120.

In an alternative embodiment of the present invention, second reaming head 110 can be fixedly attached or integrally formed with shaft 102, disposed at a fixed distance from drilling head 108, so that during the drilling procedure, the enlarged bore portion is created at a pre-defined drilling depth.

In this operative orientation shown in FIG. 8, the second reaming head 110 still does not engage bone 202, thus only bore 200 having the diameter D1 is formed in the bone 202.

It is appreciated that the second reaming head 110 can be positioned along shaft 102 in a variety of ways, such as for example, slidably loading through the proximal end 104 of the shaft 102, loading from the side such that second reaming head 110 is snapped onto shaft 102 at a particular location or by a threading engagement between shaft 102 and second reaming head 110. Reference is now made to FIG. 9, which is a simplified illustration of an example of a fourth operative stage of the Multiple Headed Drill 100, showing reaming of the bone 202 of the patient using the second reaming head 110.

It is seen in the example in FIG. 9 that once the power tool further advances the Multiple Headed Drill 100 into bone 202 of the patient, the second reaming head 110 engages bone 202 and forms an enlarged bore portion 204 proximally of bore 200, using the circumferential edge 168 of cutting tooth 160 thereof. It is appreciated that the enlarged bore portion 204 having a diameter D2, which is substantially greater than diameter D1. It is appreciated that the physician controls the resulting geometry of bore 200 and enlarged bore portion 204 by positioning the second reaming head 110 at a certain distance from drilling head 108 and using the scale marks 120 provided on shaft 102.

In some embodiments and optionally, drilling head 108 and reaming head 110 comprise flutes oriented in opposite directions so that when concurrently drilling and reaming a varying diameter bore or reaming an already drilled bore with drill head 108 still in the bone, drilling head 108 will not uncontrollably widen a drilled bore when forces carried along shaft 102 as a result of reaming may urge drilling head 108 against the drilled bore wall.

Figure 10:
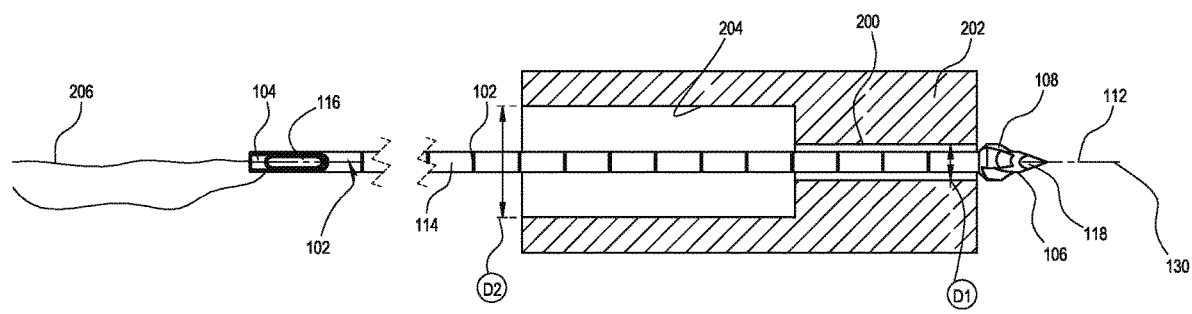
FIG. 10 is a simplified illustration of a fifth operative stage of a Multiple Headed Drill, in accordance with some embodiments of the invention.

Reference is now made to FIG. 10, which is a simplified illustration of an example of a fifth operative stage of the Multiple Headed Drill 100, showing the second reaming head 110 removed from the shaft and the resulting bore geometry within the bone 202 of the patient.

It is seen in the example in FIG. 10 that upon retraction of shaft 102 proximally, the second reaming head 110 can be removed from shaft 102 and the resulting drilled bore has a bore portion 200 having a diameter D1 and enlarged bore portion 204 having a diameter D2.

It is also seen that graft sutures 206 are pulled through aperture 116 in shaft 102 in order to enable insertion of a graft into enlarged bore portion 204.

In some embodiments, the marks 120 are employed in preparation of a site in bone for implantation of a graft. In one example, a method for preparation comprises measuring a length, L of a graft to be implanted. Providing a shaft having a distal drilling tip or a drilling end comprising a shaft pointed tip and a mounted drilling head as described elsewhere herein and one or more scale marks. In some embodiments, the method comprises drilling a bore in the bone to a desired depth. In some embodiments, the method comprises mounting at least one reaming head on the shaft so that the distal edge of the head abuts an entry hole in the surface of the bone.

In some embodiments, the method comprises measuring a distance, d proximally on the shaft from the surface entry hole of the drilling tool that corresponds to the measured graft length, L an identified by a scale mark on the shaft and then continuing drilling to a point at which the identified scale mark reaches the entry hole in the surface of the bone indicating a second depth equal to the distance, d and equal to measured length, L.

Figure 11:
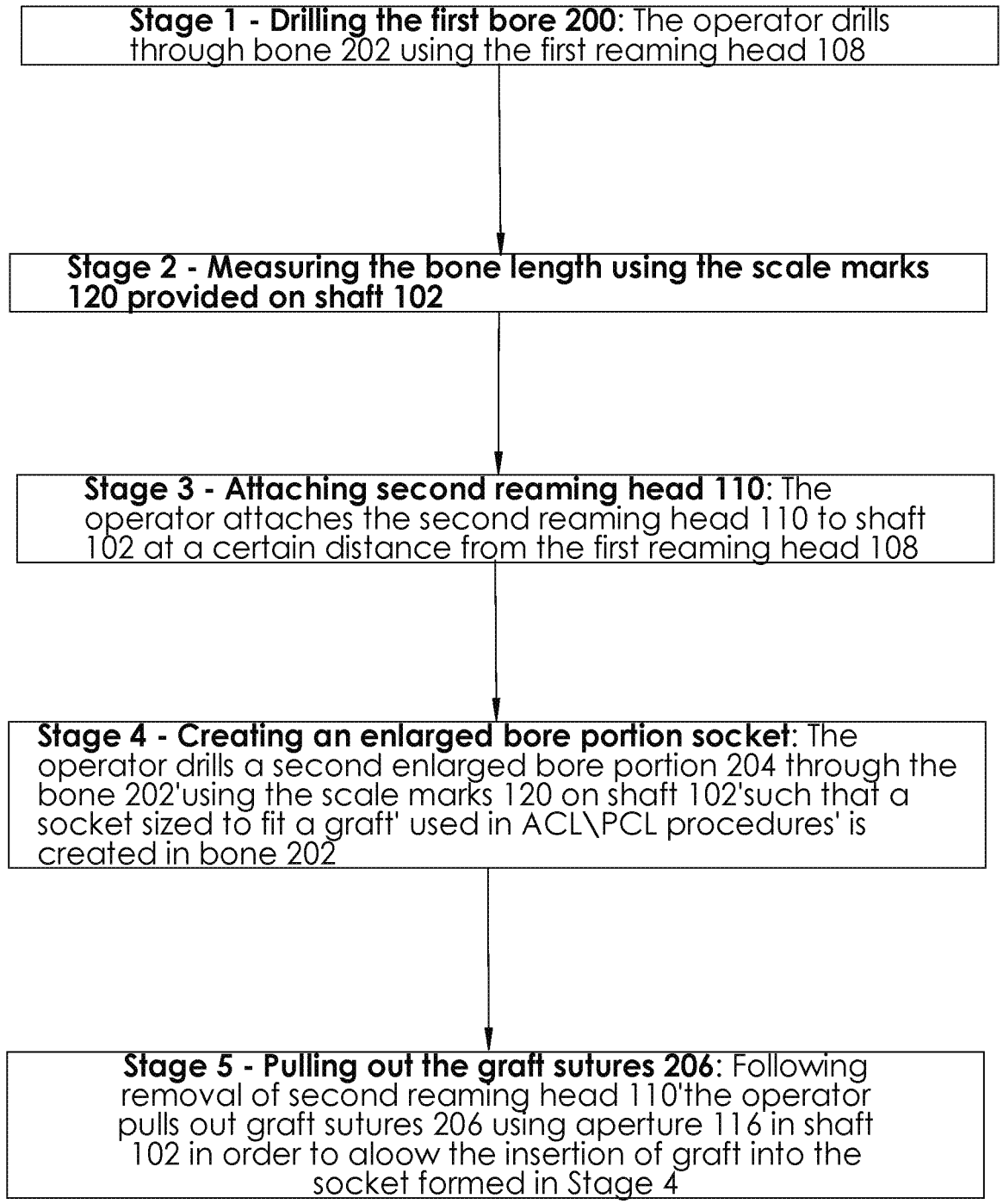
FIGS. 11, 12 and 13 are simplified flow charts illustrating methods of use of a Multiple Headed Drill similar to the drill depicted in FIGS. 1A-G and in accordance with some embodiments of the current invention.

In some embodiments, the method comprises drilling a bore to a point until the drilling tip of the shaft forms an exit hole in a surface of the bone opposite to the entry hole side of the bone. In some embodiments, the reaming head is positioned along the shaft so that a distal edge of the reaming head is disposed against the surface of the bone. The method comprises continuing to drill through the bone until a scale mark indicates that a distance from the drilling tip to the exit hole of the drilling tool is distance, d and equal to measured length, L. FIG. 11 shows a simplified flow chart illustrating an exemplary method of use of the Multiple Headed Drill 100 of FIGS. 1A-G.

Figure 12:
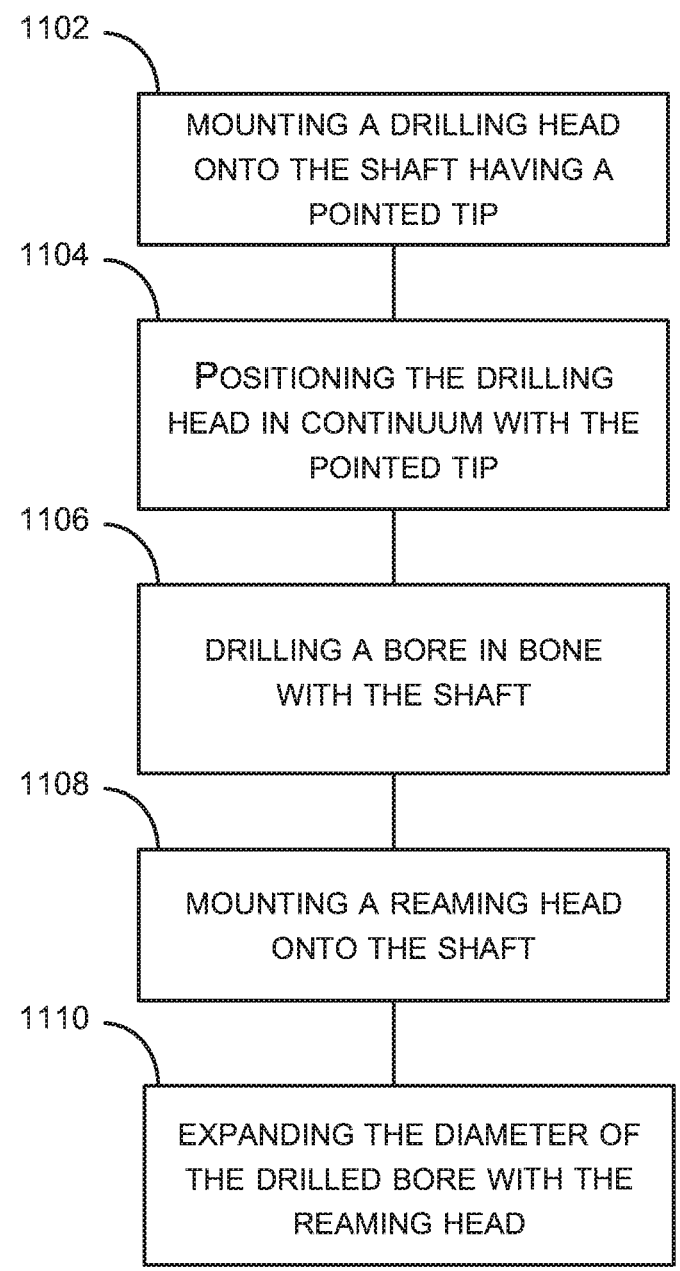

The method in the example of FIG. 11 comprises in Stage 1—drilling the first bore 200—the operator drills through bone 202 using the first reaming head 108. At Stage 2—measuring the bone length using the scale marks 120 provided on shaft 102. At Stage 3—Attaching second reaming head 110—the operator attaches the second reaming head 110 to shaft 102 at a certain distance from the first reaming head 108 and at Stage 4—Creating an enlarged bore portion socket—the operator drills a second enlarged bore portion 204 through the bone 202, using the scale marks 120 on shaft 102, such that a socket sized to fit a graft, used in ACL/PCL procedures, is created in bone 202. At Stage 5—Pulling out the graft sutures 206—Following removal of second reaming head 110—the operator pulls out graft sutures 206 using aperture 116 in shaft 102 in order to allow the insertion of a graft into the socket formed in Stage 4. FIG. 12 depicts a method of employing a Multiple Headed Drilling tool disclosed elsewhere herein comprising at 1102 mounting a drilling head onto a shaft having a pointed tip, at 1104 positioning the drilling head in continuum with the pointed tip. In accordance with the exemplary method in FIG. 12, the method further comprises at 1106 drilling a bore in bone with the shaft to a predetermined depth. At 1108 mounting a reaming head having a diameter larger than the diameter of the drilling head onto the shaft and at 1110 reaming and expanding the diameter of the drilled bore.

Figure 13:
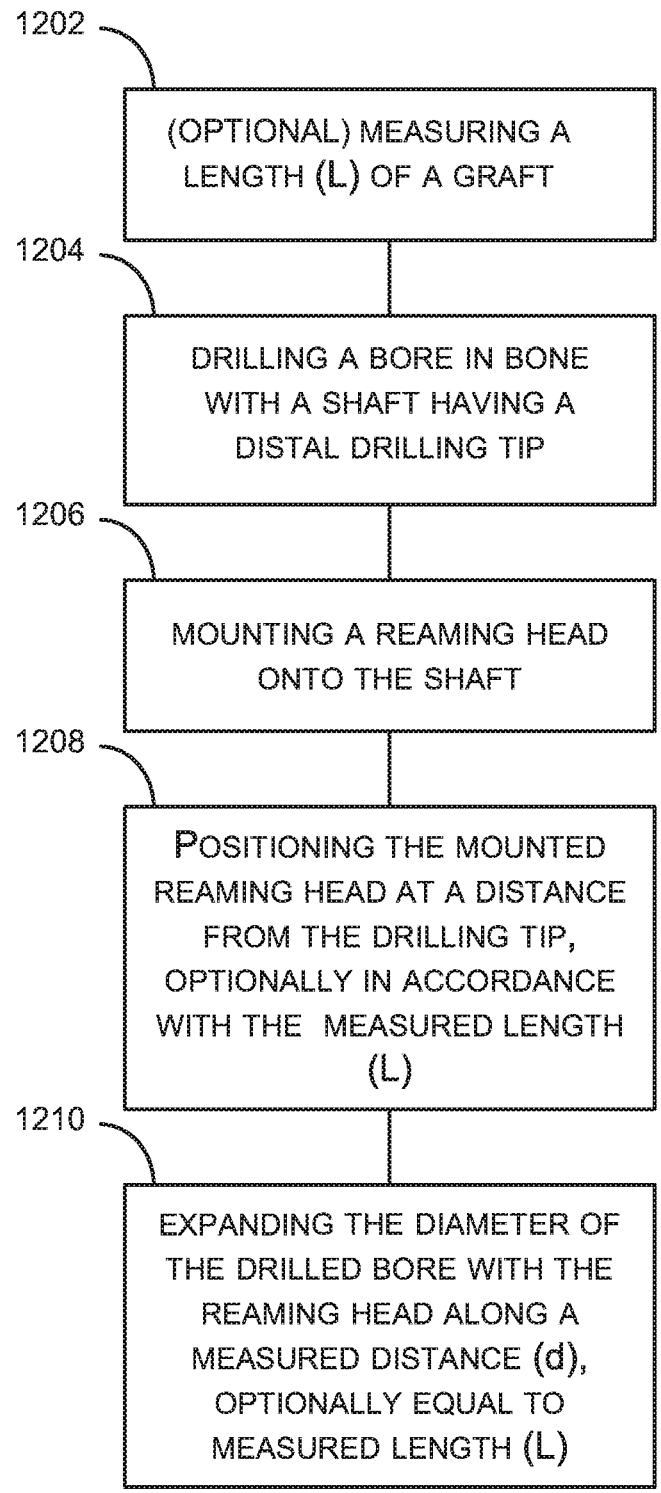

The simplified flow chart depicted in FIG. 13 depicts a method for preparing a site for implantation of a graft in bone, comprising optionally measuring a length, L of a graft to be implanted at 1202. At 1204 providing a shaft having at least one distal drilling tip and drilling a bore in bone. At 1206 mounting one or more reaming heads onto the shaft and at 1208 positioning the mounted reaming head at a distance from the drilling tip. Optionally, positioning the reaming head at a distance from the drilling tip in accordance with the measured length, L and at 1210 expanding the diameter of the drilled bore along a measured distance, d optionally equal to measured length, L.

In some embodiments, an aspect of the invention relates to a bone drilling tool kit that comprises one or more bone drill tools and a plurality of shafts 102 having a variety of pointed and/or drilling tips as disclosed elsewhere herein. In some embodiments, the shafts comprise varying diameters. In some embodiments, one or more shafts comprise scale marks 120. In some embodiments, one or more of the shafts comprise a proximal aperture 116.

In some embodiments, the kit comprises a plurality of drilling heads 108 and/or reaming heads 110 of varying diameters. In some embodiments, one or more of the drilling heads and/or reaming heads comprise different locking systems.

In some embodiments, the kit comprises a dedicated reamer/drilling head fixing tool (e.g., crimping tool) to fix one or more drilling and/or reaming heads to one or more of the shafts.

In some embodiments, the kit comprises drill tools comprising shafts comprising one or more integral reaming and/or drilling heads located at a variety of locations along the shaft and having a variety of diameters.

It is a particular feature of an embodiment of the present invention that a single tool is used during the entire surgical procedure, which is configured to enable creation of a socket for placement of a graft.

It is appreciated that drilling head 108 and second reaming head 110 may form any bore diameter, such that the diameter of bore 204 formed by second reaming head 110 is greater than the diameter of bore 200 formed by the drilling head 108.

The terms "comprises", "comprising", "includes", "including", "has", "having" and their conjugates mean "including but not limited to".

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A drill device for drilling a bore in a bone, comprising:
    a shaft having a proximal end and a distal end;
    at least one first bone cutting head positionable along said shaft adjacent said distal end; and
    at least one second bone cutting head configured to be positionable along said shaft at a location axially and proximally spaced from said first bone cutting head;
    wherein one of said bone cutting heads comprises an axially oriented hollow and at least one radially oriented through-hole that communicates with said hollow;
    wherein said device comprises a lock that fixes one of said bone cutting heads to said shaft; and wherein a surface of said shaft comprises at least one notch, and wherein said lock comprises a slotted fixing pin sized and fitted to be received in said radially oriented through-hole and one of said at least one notch in said shaft surface.

2. A drill device according to claim 1, wherein a diameter d1 of said first bone cutting head is smaller than a diameter d2 of said second bone cutting head.

3. A drill device according to claim 1, wherein said first bone cutting head is configured to drill a bore having a diameter d1 in the bone, a portion of the bore having a diameter d2 along a length L of the bore determined by a position of said second bone cutting head along said shaft.

4. A drill device according to claim 1, wherein a distal tip of said shaft is sharp and a distal edge of said first bone cutting head is positioned in continuum with said distal sharp tip to form a shaft drilling end.

5. A drill device according to claim 1, wherein said lock is configured to lock said one of said bone cutting heads at least one of axially and rotationally in respect to said shaft.

6. A drill device according to claim 1, wherein said one of said bone cutting heads comprises a threaded proximally facing recess; and wherein said shaft comprises a locking cannula threaded into said threaded proximally facing recess.

7. A drill device according to claim 6, wherein a thread of said threaded proximally facing recess is oriented in a direction opposite to a direction of rotation of said one of said bone cutting heads.

8. A drill device according to claim 1, wherein said shaft comprises at least one threaded surface segment.

9. A drill device according to claim 8, wherein at least one end of said threaded surface segment is bordered by a step.

10. A drill device according to claim 9, wherein said one of said bone cutting heads is configured to be threaded onto said shaft, wherein said threading is limited by said step.

11. A drill device according to claim 8, wherein said one of said bone cutting heads comprises an axially oriented hollow defined by a threaded wall.

12. A drill device according to claim 8, wherein a thread of said threaded segment is oriented in a direction opposite to a direction of rotation of said one of said bone cutting heads.

13. A drill device according to claim 1, wherein said proximal end of said shaft comprises at least one aperture.

14. A drill device according to claim 1, wherein flutes of said first bone cutting head are oriented in an opposite direction to flutes of said second bone cutting head.

15. A drill device according to claim 1, wherein said first and/or second bone cutting heads are positionable between 20 and 60 mm along said shaft.

16. A drill device kit comprising the drill device according to claim 1, said kit comprising:
at least one additional shaft having a proximal end and a distal end;
a plurality of additional bone cutting heads each configured to be positioned along one of said shaft and said at least one additional shaft, said plurality of additional bone cutting heads including at least one additional first bone cutting head configured to be positioned along one of said shaft and said at least one additional shaft adjacent said distal end; and
at least one additional second bone cutting head configured to be positioned along one of said shaft and said at least one additional shaft at a location axially proximally spaced from said first bone cutting head.

17. A kit according to claim 16, wherein said kit comprises a dedicated bone cutting head fixing tool configured to fix one or more of said bone cutting heads and said additional bone cutting heads, each to one of said shaft and said at least one additional shaft.

18. A kit according to claim 16, wherein said kit comprises at least one drilling tool, wherein at least one said shaft comprises a plurality of integral bone cutting heads located at a variety of locations along the said shaft and having a variety of diameters.

19. A kit according to claim 16, wherein at least one of said plurality of additional bone cutting heads is one of a drilling head and a reaming head.

20. A drill device for drilling a bore in a bone, comprising:
a shaft having a proximal end and a distal end;
at least one first bone cutting head positionable along said shaft adjacent said distal end; and
at least one second bone cutting head configured to be positionable along said shaft at a location axially and proximally spaced from said first bone cutting head;
wherein one of said bone cutting heads comprises an axially oriented hollow and at least one radially oriented through-hole that communicates with said hollow;
wherein said device comprises a lock that fixes one of said bone cutting heads to said shaft;
wherein said one of said bone cutting heads comprises a threaded proximally facing recess; and wherein said shaft comprises a locking cannula threaded into said threaded proximally facing recess.

21. A drill device according to claim 20, wherein a diameter d1 of said first bone cutting head is smaller than a diameter d2 of said second bone cutting head.

22. A drill device according to claim 20, wherein said first bone cutting head is configured to drill a bore having a diameter d1 in the bone, a portion of the bore having a diameter d2 along a length L of the bore determined by a position of said second bone cutting head along said shaft.

23. A drill device according to claim 20, wherein a distal tip of said shaft is sharp and a distal edge of said first bone cutting head is positioned in continuum with said distal sharp tip to form a shaft drilling end.

24. A drill device according to claim 20, wherein said lock is configured to lock said one of said bone cutting heads at least one of axially and rotationally in respect to said shaft.

25. A drill device according to claim 20, wherein a surface of said shaft comprises at least one notch, and wherein said lock comprises a slotted fixing pin sized and fitted to be received in said radially oriented through-hole and one of said at least one notch in said shaft surface.

26. A drill device according to claim 20, wherein a thread of said threaded proximally facing recess is oriented in a direction opposite to a direction of rotation of said one of said bone cutting heads.

27. A drill device according to claim 20, wherein said shaft comprises at least one threaded surface segment.

28. A drill device according to claim 27, wherein at least one end of said threaded surface segment is bordered by a step.

29. A drill device according to claim 28, wherein said one of said bone cutting heads is configured to be threaded onto said shaft, wherein said threading is limited by said step.

30. A drill device according to claim 27, wherein said one of said bone cutting heads comprises an axially oriented hollow defined by a threaded wall.

31. A drill device according to claim 27, wherein a thread of said threaded segment is oriented in a direction opposite to a direction of rotation of said one of said bone cutting heads.

32. A drill device according to claim 20 wherein said proximal end of said shaft comprises at least one aperture.

33. A drill device according to claim 20 wherein flutes of said first bone cutting head are oriented in an opposite direction to flutes of said second bone cutting head.

34. A drill device according to claim 20, wherein said first and/or second bone cutting heads are positionable between 20 and 60 mm along said shaft.

35. A drill device for drilling a bore in a bone, comprising:
a shaft having a proximal end and a distal end;
at least one first bone cutting head positionable along said shaft adjacent said distal end; and
at least one second bone cutting head configured to be positionable along said shaft at a location axially and proximally spaced from said first bone cutting head;
wherein one of said bone cutting heads comprises an axially oriented hollow and at least one radially oriented through-hole that communicates with said hollow;
wherein said device comprises a lock that fixes one of said bone cutting heads to said shaft;
wherein said shaft comprises at least one threaded surface segment.

36. A drill device for drilling a bore in a bone, comprising:
a shaft having a proximal end and a distal end;
at least one first bone cutting head positionable along said shaft adjacent said distal end; and
at least one second bone cutting head configured to be positionable along said shaft at a location axially and proximally spaced from said first bone cutting head;
wherein one of said bone cutting heads comprises an axially oriented hollow and at least one radially oriented through-hole that communicates with said hollow;
wherein said proximal end of said shaft comprises at least one aperture.

37. A method for drilling a bore in bone, comprising:
positioning at least one reaming head along a shaft having a drilling end, wherein at least one of said at least one reaming head comprises at least one axially oriented hollow and at least one radially oriented through-hole that communicates with said hollow;
drilling a bore in bone with the drilling end having a diameter, d1; and
employing said reaming head and expanding said diameter, d1 of said drilled bore to a larger diameter, d2;
providing a lock that fixes one of said at least one reaming head to said shaft; and
wherein a surface of said shaft comprises at least one notch, and wherein said lock comprises a slotted fixing pin sized and fitted to be received in said radially oriented through-hole and one of said at least one notch in said shaft surface.

38. A method according to claim 37, wherein said positioning comprises
moving said reaming head to a location along said shaft; and
fixedly coupling said at least one reaming head to said shaft at said location.

39. A method according to claim 38, wherein said at least one reaming head comprises a hollow configured to receive said shaft and said fixedly coupling comprises positioning said shaft within said hollow and aligning said radially oriented through hole in said at least one reaming head with a notch on a surface of said shaft and driving said fixing pin through said through hole and said notch.

* * * * *